United States Patent
Bragg et al.

(10) Patent No.: US 9,718,791 B2
(45) Date of Patent: Aug. 1, 2017

(54) FACILE METHOD FOR PREPARATION OF SODIUM 5-NITROTETRAZOLATE USING A FLOW SYSTEM

(71) Applicant: Pacific Scientific Energetic Materials Company, Chandler, AZ (US)

(72) Inventors: Jon G. Bragg, Phoenix, AZ (US); Jason B. Pattison, Phoenix, AZ (US); John W. Fronabarger, Sun Lakes, AZ (US); Michael D. Williams, Gilbert, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 0 days.

(21) Appl. No.: 15/000,444

(22) Filed: Jan. 19, 2016

(65) Prior Publication Data
US 2016/0207892 A1    Jul. 21, 2016

Related U.S. Application Data

(60) Provisional application No. 62/104,240, filed on Jan. 16, 2015.

(51) Int. Cl.
*C07D 257/06* (2006.01)
*B01J 19/24* (2006.01)
*C07D 257/04* (2006.01)

(52) U.S. Cl.
CPC ............ *C07D 257/06* (2013.01); *B01J 19/24* (2013.01); *C07D 257/04* (2013.01); *B01J 2219/24* (2013.01)

(58) Field of Classification Search
CPC ...... C07D 257/06; C07D 257/04; B01J 19/24; B01J 2219/24
USPC ........................................................ 548/400
See application file for complete search history.

(56) References Cited

U.S. PATENT DOCUMENTS

| | | |
|---|---|---|
| 2,066,954 A | 1/1937 | Von Herz |
| 3,054,800 A | 9/1962 | Burchfield et al. |
| 3,111,524 A | 11/1963 | Wiley et al. |
| 4,093,623 A | 6/1978 | Gilligan et al. |
| 4,094,879 A | 6/1978 | Bates et al. |
| 4,552,598 A | 11/1985 | Lee et al. |
| 6,375,871 B1 | 4/2002 | Bentsen et al. |
| 6,437,104 B1 | 8/2002 | Nickel et al. |
| 6,469,147 B2 | 10/2002 | Nickel et al. |
| 6,495,016 B1 | 12/2002 | Nawracala |
| 6,648,015 B1 | 11/2003 | Chow et al. |
| 6,737,026 B1 | 5/2004 | Guan et al. |
| 7,253,288 B2 | 8/2007 | Renz et al. |
| 2007/0161801 A1 | 7/2007 | Renz et al. |
| 2014/0206885 A1 | 7/2014 | Fronabarger et al. |
| 2015/0361057 A1 | 12/2015 | Bottaro et al. |

FOREIGN PATENT DOCUMENTS

| | | |
|---|---|---|
| WO | 0159013 | 8/2001 |
| WO | 03037502 | 5/2003 |
| WO | 2006029193 | 3/2006 |
| WO | 2014116654 | 7/2014 |

OTHER PUBLICATIONS

C. Galli, "Substituent Effects on the Sandmeyer reaction. Quantitative Evidence for Rate-determining Electron Transfer" J. Chem. Soc. Perkin Trans. II, 1984, pp. 897-902.
Ahn et al., "Centrifugal Gas-Liquid Separation Under Low Gravity Conditions", Lab-On-A-Chip vol. 4, Jun. 2000, pp. 121-129.
Amon et al., "Direct Methanol Micro Fuel Cell for Powering Micro Sensors", http://www.drapa.mil/mto/mpg/summaries/2003.sub--1/cmu.html, 2003, 3 pages.
Brooks et al., "Component Development for a Microchannel in Situ Propellant Production System", AIChE 2002 Spring National Meeting, Mar. 10-14, 2002, 11 pages.
Dimian et al., Integrated Design and Simulation of Chemical Processes, Chemical-Aided Chemical Engineering, vol. 35, 2nd Edition, 2014, 12 pages.
Doyle et al., "Alkyl Nitrite-Metal Halide Deamination Reactions. 2. Substitutive Deamination of Arylamines by Alkyl Nitrites and Copper(II) Halides. A Direct and Remarkably Efficient Conversion of Arylamines to Aryl halides", J. Org. Chem., vol. 42, No. 14, 1977, pp. 2426-2431.
Fortt et al., "Continuous-Flow Generation of Anhydrous Diazonium Species: Monolithic Microfluidic Reactors for the Chemistry of Unstable Intermediates", Org. Proc. Res. Dev., vol. 7, No. 5, 2003, pp. 762-768.
Gunther et al., "Transport and Reaction in Microscale Segmented Gas-Liquid Flow", Lab-on-a-Chip, vol. 4, 2004, pp. 278-286.
Gutmann et al., "Synthesis of 5-Substituted 1 H-Tetrazoles from Nitriles and Hydrazoic Acid by Using a Safe and Scalable High-Temperature Microreactor Approach", Angewandte Chemie International Edition, vol. 49, 2010, pp. 7101-7105.
Klapoetke et al., "Preparation of High Purity Sodium 5-Nitrotetrazolate (NaNT): An Essential Precursor to the Environmentally Acceptable Primary Explosive, DBX-1", Z. Anorg. Allg. Chem , vol. 639 ,(5), Mar. 15, 2013, pp. 681-688.
Klapotke et al., "Simple, Nitrogen-Rich, Energetic Salts of 5-Nitrotetrazole", Inorg. Chem., vol. 47, No. 13, Jun. 7, 2008, pp. 6014-6027.
Kralj , "Preparation of Sodium Nitrotetrazolate Using Microreactor Technology", American Institute of Aeronautics and Astronautics, Jul. 10-13, 2005, 6 pages.
Lowe et al., "Flow chemistry: Imidazole-Based Ionic Liquid Syntheses in Micro-Scale", Chemical Engineering Journal, 163 (3), 2010, pp. 429-437.

(Continued)

*Primary Examiner* — Kristin Vajda
(74) *Attorney, Agent, or Firm* — Kilpatrick Townsend & Stockton LLP

(57) ABSTRACT

Described are methods for preparing salts of 5-nitrotetrazolate that include reacting aqueous solutions of 5-aminotetrazole, an acid, and sodium nitrite in a continuous flow system at an ambient temperature.

20 Claims, 4 Drawing Sheets

(56) References Cited

OTHER PUBLICATIONS

Tegrotenhuis et al., "Normal Gravity Testing of a Microchannel Phase Separator for Insitu Resource Utilization", NASA/Cr-2001-210955, Jun. 2001, 22 pages.
Wootton et al., "On-Chip Generation and Reaction of Unstable Intermediates—Monolithic Nanoreactors for Diazonium Chemistry: Azo dyes", Lab Chip vol. 2, No. 1, pp. 5-7, Jan. 22, 2002.
International Search Report and Written Opinion, PCT Application No. PCT/US2016/013858, mailed Apr. 6, 2016.

FACILE METHOD FOR PREPARATION OF SODIUM 5-NITROTETRAZOLATE USING A FLOW SYSTEM

CROSS-REFERENCE TO RELATED APPLICATIONS

This application claims the benefit of U.S. Provisional Application Ser. No. 62/104,240, filed Jan. 16, 2015, titled "Facile Method for Preparation of Sodium 5-Nitrotetrazolate Using a Flow System," the entire contents of which are hereby incorporated by reference.

FIELD OF THE INVENTION

The present invention is directed to the field of substituted tetrazole synthesis and manufacture. More particularly, the present invention is directed to processes for preparing substituted tetrazoles and tetrazolate salts, such as sodium 5-nitrotetrazolate, utilizing flow chemistry techniques. The use of the present technique results in less hazardous, more efficient large scale manufacturing processes.

BACKGROUND

Sodium 5-nitrotetrazolate ("NaNT," 6) has found application as a reactant or constituent in a variety of explosives and propellants and additional uses are contemplated. Typically, NaNT is synthesized via a Sandmeyer type reaction that involves displacement of a diazonium group by a nucleophile, in this case nitrite ion resulting in a nitro group, in the presence of cupric salts. C. Galli, "Substituent Effects on the Sandmeyer reaction. Quantitative Evidence for Rate-determining Electron Transfer," *J. Chem. Soc. Perkin Trans. II*, No. 5, 1984, pp. 897-902; U.S. Pat. No. 4,093,623. Energetics chemists have been utilizing this method for a number of years to produce NaNT in small batches.

This procedure, outlined in FIG. 1, involves addition of a solution of commercially available 5-aminotetrazole ("5-AT," 1) in aqueous nitric acid to a solution of copper(II) sulfate and sodium nitrite to generate the diazonium ion (3), which undergoes substitution to afford the acid copper salt of 5-nitrotetrazole ("5-NT," 5). During the addition of the 5-AT and nitric acid, the reaction temperature must be tightly controlled at or below 18° C. due to the thermal instability of the diazonium intermediate. The second process step utilizes aqueous sodium hydroxide to convert the acid copper salt of 5-NT into NaNT and generates copper oxide as a byproduct.

This method is problematic, particularly during larger scale procedures, due to "micro-detonations," which occur if the mixing of the 5-AT and sodium nitrite solutions is not tightly controlled. These micro-detonations may be caused by nitrogen oxide fumes from the reaction solution reacting with droplets of 5-AT on surfaces in the reactor to form 5-diazotetrazole (4), which may spontaneously detonate in solution when the concentration exceeds 1%.

These micro-detonations may be strong enough to break glass and may result in release of the potentially explosive reaction mixture. It was determined that inclusion of a small amount of $CuSO_4$ to the 5-AT solution prior to addition to the $CuSO_4$-nitrite solution was effective in preventing the micro-detonations by catalyzing conversion of 5-diazotetrazole, in the presence of nitrite, to 5-NT. Use of these cupric salts, however, adds additional steps (and cost and/or time) to the procedure, which results in lower overall reaction yields. These additional operations include two manual filtration steps in which operators are exposed to considerable quantities of $CuH(5-NT)_3$ and NaNT, both of which are explosives. In considering this process, it is quite clear that a less hazardous, alternate procedure is needed for large scale laboratory production of NaNT.

As opposed to batch processes, such as those described in U.S. Pat. Nos. 3,054,800 and 3,111,524, this invention provides a simple, continuous flow process for the synthesis of 5-nitrotetrazolates starting from 5-AT, which is converted directly, via an ambient temperature Sandmeyer reaction, to a salt of 5-nitrotetrazolate without the use of copper, as illustrated in FIG. 4.

U.S. Pat. No. 7,253,288 to R. N. Renz, M. D. Williams, and J. W. Fronabarger, also describes an alternate method for producing NaNT utilizing microreactor technology, which does not use copper to stabilize the tetrazole diazonium intermediate and which involves direct reaction of 5-AT/nitric acid with sodium nitrite at ambient temperature in a continuous flow regime. Unlike a batch process, this procedure generates only very small amounts of the unstable reaction intermediates in a dilute media, which are subsequently consumed via substitution as a part of the flow process. This process provides a safe method for preparation of 5-nitrotetrazolates, as only minor amounts of the intermediates are generated per unit time and accumulation is not possible, but requires extensive time and an appropriate microreactor system optimized for 5-NT production for the flow process.

U.S. Publication No. 2014/0206885 also describes a continuous flow process for production of 5-nitrotetrazolates, which does not use copper to stabilize the diazonium intermediate reactant and involves direct reaction of 5-AT/nitric acid with sodium nitrite at an elevated reaction temperature to promote expedient substitution of the nitro group in place of the diazo group and to ensure rapid consumption of hazardous reactants. However, because the diazonium intermediate becomes unstable at higher reaction temperatures, instead of being quickly converted into the desired 5-NT, the diazonium intermediate may in certain infrequent cases instead form minor amounts of 5-azidotetrazole, which is a highly explosive and undesirable side product. As a result, the final product may have an undesirable purity profile and additional purification steps may be required.

The methods for preparation of 5-nitrotetrazolate salts outlined above may be prohibitive either in terms of time and safety for the batch process and/or for possessing an appropriate microreactor system optimized for 5-NT production for the flow process. There is a need to improve the efficiency and safety of the chemical process by providing a method for preparation of 5-nitrotetrazolate salts, specifically NaNT, quickly from 5-AT and utilizing a method in which all of the unstable intermediates are quickly and fully consumed at ambient temperatures.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the invention, a method for preparing salts of 5-nitrotetrazolate comprises reacting aqueous solutions of 5-aminotetrazole, an acid, and sodium nitrite in a continuous flow system at ambient temperature, which in some embodiments may be in a range of approximately 10° C. to approximately 50° C., or may be in a range of approximately 20° C. to approximately 30° C.

In certain embodiments, the sodium nitrite is added in excess to control pH within a pH range of approximately 4 to approximately 5. The acid may comprise nitric acid, sulfuric acid, or perchloric acid.

The 5-aminotetrazole and the acid may comprise one reactant stream, and the sodium nitrite may comprise a second reactant stream.

The continuous flow system may further comprise a processing zone that is held at the ambient temperature. The processing zone may comprise a mixing zone that combines the first reactant stream and the second reactant stream into a reactant mixture and a reaction zone that is configured to retain the reactant mixture in the reaction zone until the reaction is complete. In some embodiments, the reaction zone retains the reactant mixture in the processing zone until a product with at least 60% yield of sodium 5-nitrotetrazolate is achieved.

In some embodiments, the product may be produced at a rate of at least 100 g/hour.

According to certain embodiments of the present invention, a reaction product of 5-aminotetrazole, an acid, and sodium nitrite is prepared via a continuous flow system at ambient temperature, wherein the reaction product comprises at least 60% yield of sodium 5-nitrotetrazolate.

According to certain embodiments of the present invention, a continuous flow system for preparing salts of 5-nitrotetrazolate comprises a first reactant stream comprising 5-aminotetrazole and an acid, and a second reactant stream comprising sodium nitrite, a mixing zone that combines the first reactant stream and the second reactant stream into a reactant mixture, and a reaction zone that is configured to retain the reactant mixture at a constant temperature until the reaction is complete. The acid may comprise nitric acid, sulfuric acid, or perchloric acid.

The mixing zone and the reaction zone may be held at the ambient temperature in a range of approximately 10° C. to approximately 50° C., or may be held at the ambient temperature in a range of approximately 20° C. to approximately 30° C. The reaction zone may retain the reactant mixture until a product with at least 60% yield of sodium 5-nitrotetrazolate is achieved.

According to certain embodiments of the present invention, a method for preparing a salt of 5-nitrotetrazolate comprises (a) mixing an aqueous solution of 5-aminotetrazole and an acid with an aqueous solution of a nitrite salt in a continuous flow system to form a reactant mixture, (b) retaining the reactant mixture in a processing zone of the continuous flow system at a constant temperature, (c) forming an aqueous product within the reaction zone, and (d) collecting the aqueous product. In some embodiments, the constant temperature may be in a range of approximately 10° C. to approximately 50° C., or may be in a range of approximately 20° C. to approximately 30° C.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 4:
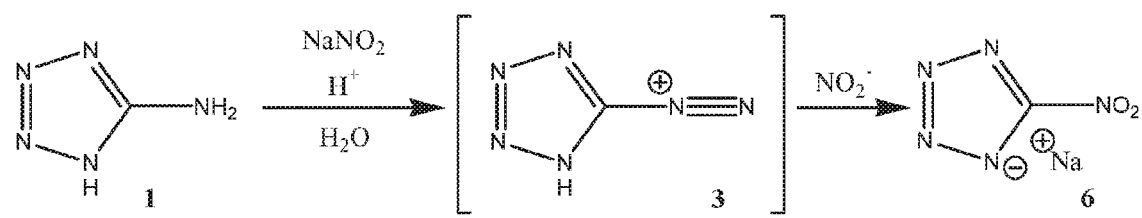
FIG. 4 is a depiction of a method used for preparation of NaNT, according to certain embodiments of the present invention.

According to certain embodiments, as best illustrated in FIG. 4, a process has been developed to prepare high purity NaNT by combining the reactants at ambient temperature. The process provides facile access to a high purity, concentrated aqueous solution of NaNT, which may be directly utilized in subsequent reactions or isolated as an end product.

Figure 1:
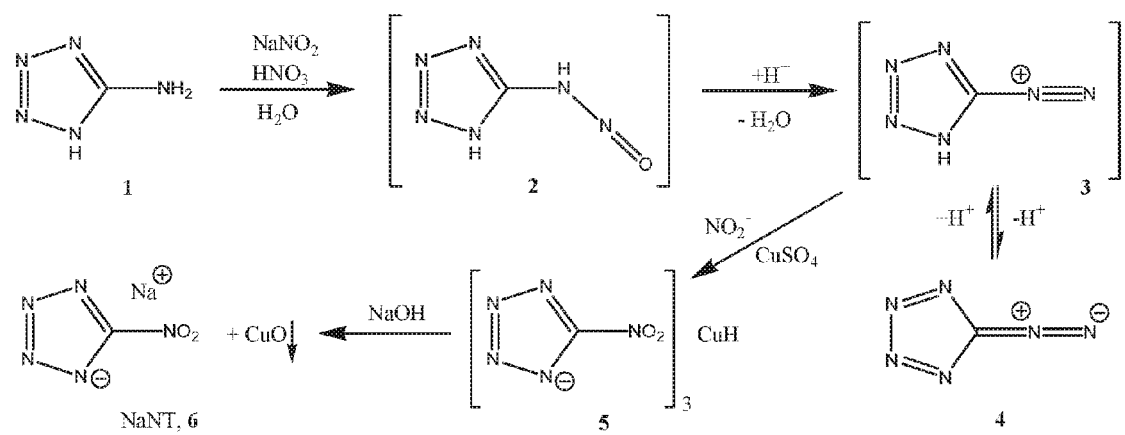
FIG. 1 is a depiction of certain intermediates formed during preparation of NaNT, according to certain prior art methods.
Figure 2:
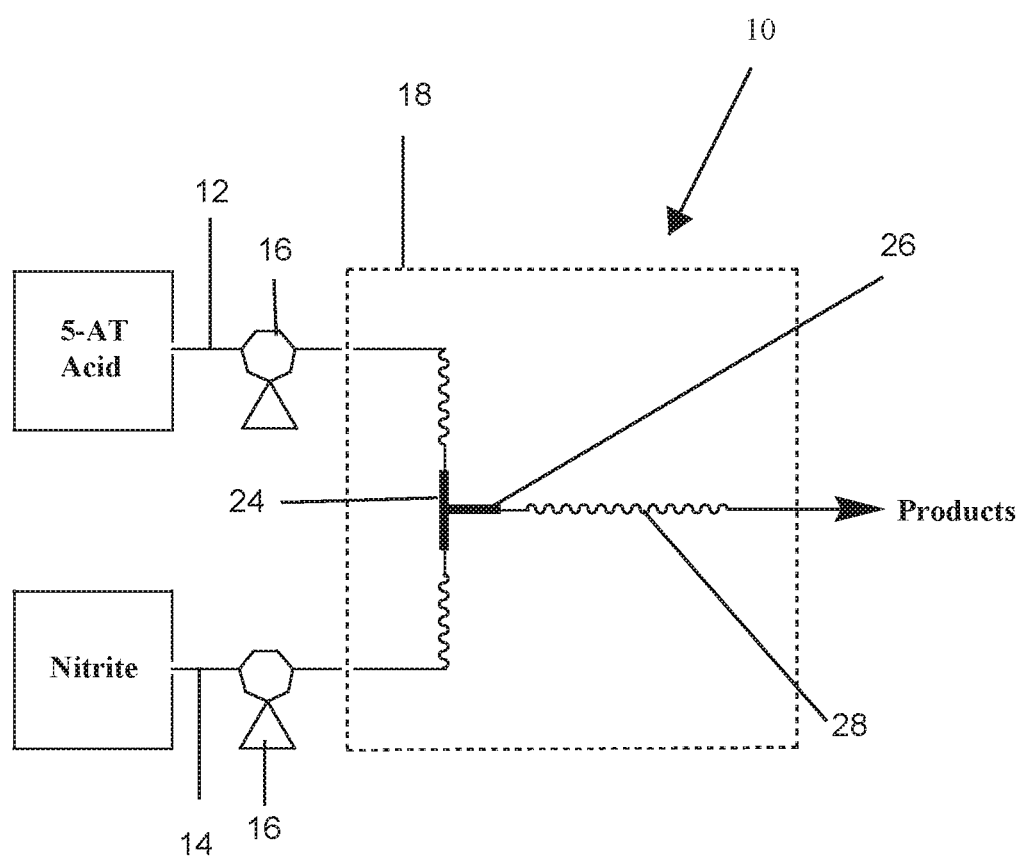
FIG. 2 is a flow diagram of a method used for preparation of NaNT, according to certain embodiments of the present invention.
Figure 3:
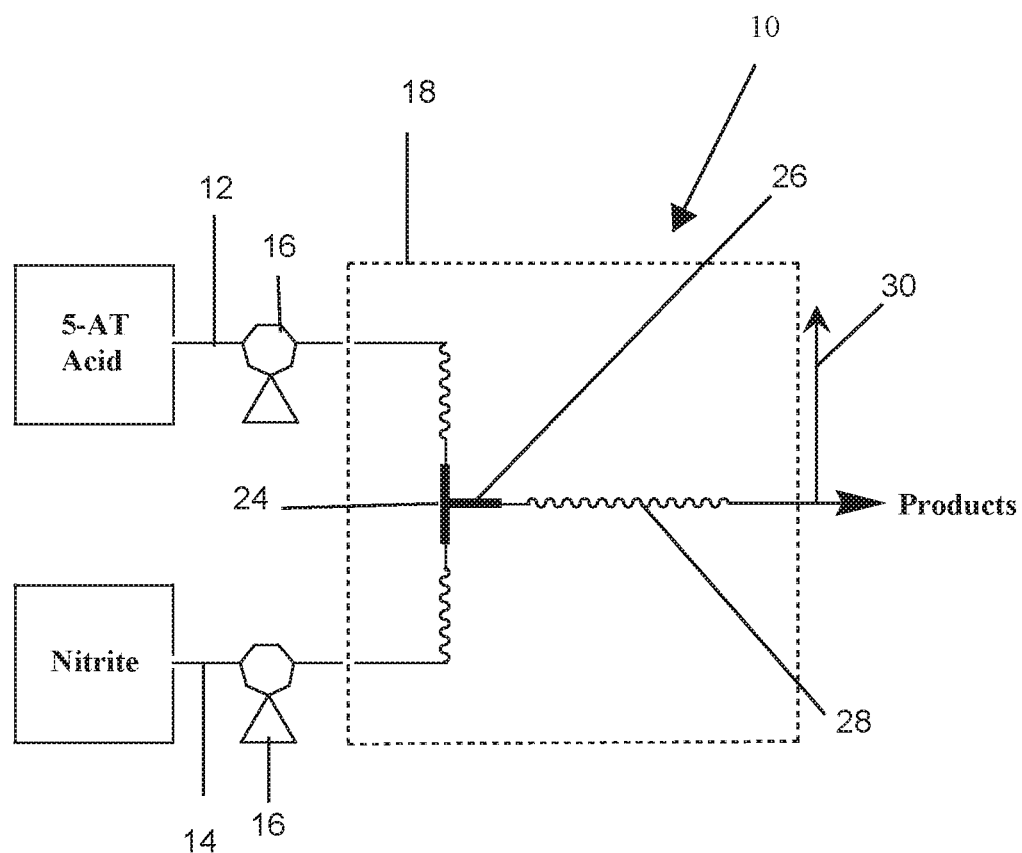
FIG. 3 is a flow diagram of a method used for preparation of NaNT, according to certain embodiments of the present invention.

According to certain embodiments of the present invention, NaNT is prepared utilizing a continuous flow system 10, such as the embodiments illustrated in FIGS. 2 and 3. In these embodiments, NaNT may be prepared by reacting aqueous solutions of 5-AT, a suitable acid such as nitric, sulfuric or perchloric acid, and sodium nitrite in the continuous flow system 10. The components may be reacted under conditions suitable to synthesize a high purity, concentrated aqueous solution of NaNT.

In certain embodiments, as illustrated in FIGS. 2 and 3, the components may be introduced into the continuous flow system 10 by mixing water, 5-AT, and an appropriate acid to form a first reactant stream 12, and adding an aqueous solution of an appropriate nitrite as a second reactant stream 14. In other embodiments, each reactant may be separately introduced into the continuous flow system 10.

The acid may be selected from any known acid or mixture of acids that will, when mixed with 5-AT and a nitrite, facilitate substitution of the nitro group in place of the diazo group in the diazonium intermediate. Most strong inorganic acids are suitable for use in the present invention. Non-limiting examples would include nitric, sulfuric, or perchloric acids. Similarly, the nitrite may be selected from any known nitrite or mixture of nitrites that will, when mixed with 5-AT and an acid, facilitate substitution of the nitro group in place of the diazo group in the diazonium intermediate. Non-limiting examples may include sodium, potassium, or lithium nitrites.

In certain embodiments, one or more pumps 16 may be used to transport the reactant steams 12, 14 from storage tanks or vessels into the continuous flow system 10. In the current invention, peristaltic pumps are used to maintain the high flow rates required.

Downstream of the pumps 16, the reactant streams 12, 14 may separately enter a processing zone 18. As illustrated in FIGS. 2 and 3, the processing zone 18 may comprise a mixing zone 24 and/or a reaction zone 28. The processing zone 18 may be designed so that the reaction may be carried out in the processing zone 18 with an ambient temperature in a range of approximately 10° C. to approximately 50° C. Alternatively, the reaction may be performed in the processing zone 18 with an ambient temperature in a range of approximately 20° C. to approximately 30° C.

By utilizing an ambient reaction temperature, the diazonium intermediate remains stable so as to minimize side reactions that may produce hazardous and undesirable impurities in the final product. While the ambient reaction temperature may be helpful to minimize unstable side reactions of the diazonium ion, the ambient reaction temperature may also decrease the rate of substitution of nitro groups in place of the diazo groups on the diazonium ion, thus leaving an undesirable (albeit stable) impurity concentration of diazonium ions in the final product.

Other process variables may be adjusted or controlled in order to compensate for a potentially diminished rate of substitution at the ambient reaction temperature. For example, another option to achieve the desired substitution rate may be to maintain the pH of the reactant mixture 26 within a predetermined range, such as within a pH range of approximately 4 to approximately 5. Other pH ranges may be considered and not limited by the current invention; however, reacting outside of the claimed pH range will likely result in an altered impurity profile. By increasing the rate of the substitution reaction through pH control, potential impurities in the final product due to side reactions of an unstable diazonium ion and/or due to the presence of unreacted diazonium ions are minimized.

Controlling the pH within the desired range, particularly when that range is not at an exceptional low end or high end of the pH range (i.e., in the 1-2 or 12-14 pH range), is conventionally done through incorporation an additional buffering agent, which is often selected from among suitable phosphates and acetates. These buffering agents are typically chosen so that they will not to participate as a reactant in the reaction. As a result, an additional filtration or purification step is typically needed to remove the buffering agent from the final product.

To avoid introducing another potential impurity into the reaction via the buffering agent as described above, which must be removed in order to obtain a high purity, concentrated aqueous solution of NaNT, one or more of the reactants may be added at a concentration level that allows the reactant to both effect the substitution reaction to provide the desired purity and concentration of 5-nitrotetrazolate, as well as to act as a buffering agent to maintain the pH within the desired range.

For example, the nitrite may be supplied to the continuous flow system 10 in an amount sufficient to react with the acid to generate a diazonium intermediate from the 5-AT and provide sufficient excess nitrite to form 5-NT, as well as to control the pH of the reactant mixture 26 within a range of approximately 4 to approximately 5. For example, the nitrite may be supplied to the continuous flow system 10 in a molar ratio of at least 2 moles of nitrite per mole of 5-AT, up to 10 moles of nitrite per mole of 5-AT, or even greater ratios of moles of nitrite to moles of 5-AT.

Similarly, the acid may be supplied to the continuous flow system 10 in an amount sufficient to react with the nitrite to generate a diazonium intermediate from the 5-AT and provide a 5-NT. In some embodiments, the acid may also be supplied in an amount sufficient to control the pH of the reactant mixture 26 within a range of approximately 4 to approximately 5. For example, the acid may be supplied to the continuous flow system 10 in a molar ratio of at least 2 moles of protons per mole of 5-AT, up to 10 moles of protons per mole of 5-AT, or even greater ratios of moles of protons to moles of 5-AT.

In certain embodiments, all of the components of the processing zone 18 may be heated or cooled by a common heat source, such as a common water bath, oven, heat exchanger, or other heat source/sink. In other embodiments, different heat sources/sinks may be used among the mixing zone 24 and reaction zone 28 as needed and/or desired to achieve different temperatures within each area in order to further optimize the reaction within the continuous flow system 10.

For example, the first reactant stream 12 may pass into the continuous flow system 10 and the second reactant stream 14 may pass into the continuous flow system 10 prior to being combined in the mixing zone 24.

Once the reactant streams 12, 14 are introduced into the mixing zone 24, the reactant streams 12, 14 are mixed to form the reactant mixture 26. According to certain embodiments, the mixing zone 24 may be a mixing T. It is contemplated that mixing of the reactants may be performed using any type of device that would allow continuous blending or merging of the reactant streams 12, 14, including but not limited to a transfer pump, a static mixer, an oscillatory baffled reactor, a mechanical agitator, and/or a continuously stirred tank reactor. Alternatively, it is contemplated that a series of mixing devices may be used to introduce the reactants gradually via a manifold.

The reactant mixture 26 then passes from the mixing zone 24 into the reaction zone 28. According to certain embodiments, the reaction zone 28 may comprise a reaction coil of sufficient length and volume to provide a retention time in the processing zone 18 until the reaction is complete. More specifically, the reaction zone 28 may be configured to allow the reaction to proceed within the processing zone 18 until a product with at least 60% yield of NaNT is achieved, which may further range up to a 95% yield of NaNT.

Upon mixing, the combination of reactants generates large volumes of gas as a result of substitution of the diazonium species. As illustrated in FIG. 3, this gas may optionally be released using a gas/liquid separator 30 either inside or outside the processing zone 18 or, as illustrated in FIG. 2, may be confined in the flow tubing until it exits the flow reactor. The product then exits the processing zone 18, where it is collected in a suitable vessel.

In the embodiments where the nitrite reactant is added in excess for pH control, the excess nitrite is still present in the reactant mixture 26 after the substitution reaction has reached completion. To remove the excess nitrites, additional acid may be added to the reactant mixture 26 at any one or more of various suitable locations, which include but are not limited to a late stage of the reaction zone 28 at a point where the reaction is nearing or at completion; at the point where the reactant mixture 26 exits the processing zone 18; and/or after the reactant mixture 26 is being held the receiving vessel. The excess nitrite and acid forms $N_2O_3$, which then bubbles out of the reactant mixture 26, thus removing the excess nitrite as a potential impurity in the final product.

The manufacturing process depicted in FIGS. 2 and 3 may be carried out, either in whole or in part, in a flow system. It is understood that the flow system may be comprised of tubing of a composition suitable for containing the reactants at the prescribed temperatures. Additionally, the tubing may be of any diameter that allows for flow rates and retention times that provide for the rapid conversion of 5-AT to 5-NT. Similarly, it is understood that the pumping devices 16 will supply the reactants at a flow rate that allows for continuous mixing as well as a system retention time that allows for complete reaction in the processing zone 18.

It has been found that the application of the processes described herein achieves the goals of providing a process for rapid preparation of 5-nitrotetrazolates, specifically NaNT, that is both safe and more efficient than conventional processes and may be suitable for use in large scale manufacturing operations.

In particular, performance of the process at ambient temperature and use of excess nitrite for pH control within a range that increases the rate of the substitution reaction produces an aqueous product that comprises highly concentrated NaNT with minimal impurities, and which can be produced in greater quantities than are possible prior art methods. Specifically, in certain embodiments, the rate of production of product with these characteristics is at least 100 g/hour. It should be noted though, that a critical attribute of this invention is that this process is scalable to whatever production rates are necessary.

TABLE I

EL4C153-120 Solution Components

| Retention time (min) | Component ID | Area Ratio - NaNT |
|---|---|---|
| 2.8 | $NO_2^-/NO_3^-$ | 1.3906 |
| 3.1 | 1H-tetrazole | 0.0165 |
| 3.5 | tetrazole diazonium | 0.0669 |
| 3.8 | 5,5'-azotetrazole | 0.015 |
| 3.9 | 5-azidotetrazole | 0 |
| 4.0 | unknown | 0.0033 |
| 4.6 | NaNT | 1 |
| 5.8 | unknown | 0.1159 |

TABLE II

EL4M123B Solution Components

| Retention time (min) | Component ID | Area Ratio - NaNT |
|---|---|---|
| 2.8 | $NO_2^-/NO_3^-$ | 1.466 |
| 3.1 | 1H-tetrazole | 0.011 |
| 3.5 | tetrazole diazonium | 0 |
| 3.8 | 5,5'-azotetrazole | 0 |
| 3.9 | 5-azidotetrazole | 0 |
| 4.0 | unknown | 0 |
| 4.5 | NaNT | 1 |
| 5.8 | unknown | 0 |

TABLE III

| NaNT Samples | nitrate (g/mL) | nitrite | 1H-tetrazole | 5-amino-tetrazole | 5-azido-tetrazole | 5-nitramino-tetrazole | tetrazolone | bitetrazole | bitetrazole-amine |
|---|---|---|---|---|---|---|---|---|---|
| 73387 | trace | <0.001 | <0.003 | trace | ND | trace | trace | trace | ND |
| 73272 | trace | <0.001 | <0.003 | trace | ND | trace | ND | ND | ND |
| 72756 | 0.0006 | <0.001 | <0.0035 | trace | ND | trace | trace | trace | ND |
| 72757 | 0.0005 | <0.001 | <0.002 | trace | ND | trace | ND | ND | ND |
| 73213 | trace | <0.001 | <0.003 | trace | ND | trace | ND | trace | ND |
| 4M123B | 0.049 | ND | 0.0049 | ND | ND | ND | trace | trace | 0.001 |
| 4M125B | 0.055 | ND | 0.0045 | ND | ND | ND | ND | trace | 0.001 |

Tables I, II, and III list the impurity contents for NaNT produced from both prior art and the inventive method described in this application. For example, Sample EL4C153-120 listed in Table I was produced using the method outlined in U.S. Publication No. 2014/0206885. Sample EL4M123B listed in Table II was produced using the method described in this application. In Table III, Samples 73387, 73272, 72756, 72757, and 73213 were produced using a Batch-Sandmeyer Process, and Samples 4M123B and 4M125B were produced using the method described in this application.

Because of differences in the impurity profiles for NaNT produced by other methods, performing additional concentration steps on products produced from those methods may not result in a purity profile that is comparable to the purity profile of the product obtained with the present method, as illustrated in Tables II and III.

Specifically, the present method reaction product comprises at least 60% yield of sodium 5-nitrotetrazolate and with only minor amounts of other impurities as shown in Tables II and III.

Those skilled in the art will appreciate that the specifics of the processes provided may be modified, without departing from the present disclosure.

EXAMPLES

The following examples demonstrate the utility of the present processes.

Example 1

5-AT (494 g, 4.8 mol) was dissolved in 820 mL of aqueous perchloric acid (9.4 mol)—reactant stream 12. Sodium nitrite (1656 g, 24.0 mol) was dissolved in 2 L of deionized water—reactant stream 14. The reactant streams 12, 14 were pumped at a rate of 10 mL/minute into the mixing T 24. The tubing diameter was 0.125 inches (3.1 mm) (ID). The length of the tubing from the pumps 16 into the mixing T 24 was 2.5 feet and was 10.8 feet (331 cm) after the mixing T 24 and connected into a second reaction zone of tubing consisting of tubing diameter of 0.250 inches (6.35 mm) (ID) and a length of 10.3 feet (315 cm). This configuration provided a retention time of approximately 25 minutes in the processing zone 18 and a post mixing volume of approximately 500 mL. The processing zone 18 (in this case a water bath) was maintained at 20-25° C. during operation. The continuous flow system 10 was allowed to come to equilibrium for approximately 25 minutes before product was acquired.

After the product exited the processing zone 18, it was collected in an e-flask. After collecting the product, the solution was treated with a 10% by volume of 11.7 M perchloric acid to remove excess nitrite from the solution. As an example, approximately 7,750 mL of product was treated with 750 mL of 11.7 M perchloric acid, yielding a final volume of 8,500 mL. HPLC analysis of the reaction mixture indicated sodium 5-nitrotetrazolate with a concentration of 0.115 grams of NaNT per milliliter of solution, which corresponds to a yield of 73% based on 5-AT. The resulting concentrations of other constituents were nitrate ion: 0.065 grams/mL; 1H-tetrazole: 0.005 grams/mL; nitrite ion: 0 grams/mL; and 5-azidotetrazole: below the equipment's detection limit of 325 ppm. The NaNT solution obtained by this procedure was used directly in the successful preparation of Tetraammine-cis-bis[5-nitro-2H-tetrazolato-$N^2$] cobalt (III) perchlorate (BNCP) which was of superior bulk density and purity to BNCP synthesized from NaNT derived from the copper-Sandmeyer batch process. This particular lot of BNCP was further tested in its standard detonator configuration and function testing of the units produced an acceptable output.

Example 2

5-AT (123 g, 1.2 mol) was dissolved in 205 mL of aqueous perchloric acid (2.4 mol) and diluted to 1 L volume with deionized water creating a 1.2 M 5-AT solution in 2.4 M perchloric acid—reactant stream 12. Sodium nitrite (828 g, 12.0 mol) was dissolved in 1 L of deionized water creating a 12 M $NaNO_2$ solution—reactant stream 14. The reactant streams 12, 14 were pumped at a rate of 10 mL/minute into the mixing T 24. The tubing diameter was 0.125 inches (3.1 mm) (ID). The length of the tubing from the pumps 16 into the mixing T 24 was 2.5 feet and was 10.8 feet (331 cm) after the mixing T 24 and connected into a 2nd reaction zone of tubing consisting of tubing diameter of 0.250 inches (6.35 mm) (ID) and a length of 10.3 feet (315 cm). This configuration provided a retention time of approximately 25 minutes in the processing zone 18 and a post mixing volume of approximately 500 mL. The processing zone 18 (in this case a water bath) was maintained at 20-25° C. during operation. The continuous flow system 10 was allowed to come to equilibrium for approximately 25 minutes before product was acquired.

After the product exited the processing zone 18, it was collected in an e-flask. HPCL analysis of the reaction mixture indicated sodium 5-nitrotetrazolate with a concentration of 0.075 grams per milliliter of solution, indicating a yield of 72%. The resulting concentrations of other constituents were as follows: nitrate ion: 0.038 grams/mL; 1H-tetrazole: 0.004 grams/mL; nitrite ion: 0.093 grams/mL; and 5-azidotetrazole: below the equipment's detection limit of 325 ppm. The solution was then treated with a 10% by volume of 11.7M perchloric acid in a similar fashion to Example 1. After treatment, the resulting concentrations of the solution constituents are as follows; NaNT: 0.054 grams/mL; nitrate ion: 0.046 grams/mL; 1H-tetrazole: 0.003 grams/mL; nitrite ion: 0.004 grams/mL; and 5-azidotetrazole: below the equipment's detection limit of 325 ppm.

Different arrangements of the components depicted in the drawings or described above, as well as components and steps not shown or described are possible. Similarly, some features and sub-combinations are useful and may be employed without reference to other features and sub-combinations. For example, the choice of using two different tubing diameters of two different lengths or any combination of tubing diameters and lengths connected together to provide sufficient residence times to complete the conversion of 5-aminotetrazole and nitrite to form 5-nitrotetrazolate is allowable. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method for preparing salts of 5-nitrotetrazolate comprising reacting aqueous solutions of 5-aminotetrazole, an acid, and sodium nitrite in a continuous flow system at an ambient temperature, wherein the sodium nitrite is added in excess to control pH within a pH range of approximately 4 to approximately 5.

2. The method of claim 1, wherein the ambient temperature is in a range of approximately 10° C. to approximately 50° C.

3. The method of claim 1, wherein the ambient temperature is in a range of approximately 20° C. to approximately 30° C.

4. The method of claim 1, wherein the acid comprises nitric acid, sulfuric acid, or perchloric acid.

5. The method of claim 1, wherein the 5-aminotetrazole and the acid comprise a first reactant stream, and the sodium nitrite comprises a second reactant stream.

6. The method of claim 5, wherein the continuous flow system comprises a processing zone that is held at the ambient temperature.

7. The method of claim 6, wherein the processing zone comprises a mixing zone that combines the first reactant stream and the second reactant stream into a reactant mixture and a reaction zone that is configured to retain the reactant mixture in the processing zone until the reaction is complete.

8. The method of claim 7, wherein the reaction zone retains the reactant mixture in the processing zone until a product with at least 60% yield of sodium 5-nitrotetrazolate is achieved.

9. The method of claim 8, wherein the product is produced at a rate of at least 100 g/hour.

10. The method of claim 1, wherein a product is produced at a rate of at least 100 g/hour.

11. The method of claim 10, wherein the ambient temperature is in a range of approximately 10° C. to approximately 50° C.

12. The method of claim 10, wherein the ambient temperature is in a range of approximately 20° C. to approximately 30° C.

13. The method of claim 10, wherein the acid comprises nitric acid, sulfuric acid, or perchloric acid.

14. The method of claim 10, wherein the 5-aminotetrazole and the acid comprise a first reactant stream, and the sodium nitrite comprises a second reactant stream.

15. The method of claim 14, wherein the continuous flow system comprises a processing zone that is held at the ambient temperature.

16. The method of claim 15, wherein the processing zone comprises a mixing zone that combines the first reactant stream and the second reactant stream into a reactant mixture and a reaction zone that is configured to retain the reactant mixture in the processing zone until the reaction is complete.

17. A method for preparing salts of 5-nitrotetrazolate comprising reacting aqueous solutions of 5-aminotetrazole, an acid, and sodium nitrite in a continuous flow system at an ambient temperature,
wherein the 5-aminotetrazole and the acid comprise a first reactant stream, and the sodium nitrite comprises a second reactant stream,
wherein the continuous flow system comprises a processing zone that is held at the ambient temperature,
wherein the processing zone comprises a mixing zone that combines the first reactant stream and the second reactant stream into a reactant mixture and a reaction zone that is configured to retain the reactant mixture in the processing zone until the reaction is complete,
wherein the reaction zone retains the reactant mixture in the processing zone until a product with at least 60% yield of sodium 5-nitrotetrazolate is achieved, and
wherein the product is produced at a rate of at least 100 g/hour.

18. The method of claim 17, wherein the ambient temperature is in a range of approximately 10° C. to approximately 50° C.

19. The method of claim 17, wherein the ambient temperature is in a range of approximately 20° C. to approximately 30° C.

20. The method of claim 17, wherein the acid comprises nitric acid, sulfuric acid, or perchloric acid.

* * * * *